US00PP37037P2

(12) United States Plant Patent
Ohashi et al.

(10) Patent No.: US PP37,037 P2
(45) Date of Patent: Oct. 21, 2025

(54) STRAWBERRY PLANT NAMED 'HOB-R490'

(50) Latin Name: ***Fragaria* x *ananassa* Duchesne ex Rozier**
Varietal Denomination: HOB-R490

(71) Applicant: HOB Co. Ltd., Kamikawa Hokkaido (JP)

(72) Inventors: Takafumi Ohashi, Chiba (JP); Yuhei Takeda, Hokkaido (JP); Marina Iwao, Kamikawa Hokkaido (JP)

(73) Assignee: HOB Co. Ltd., Higashikagura-cho (JP)

( * ) Notice: Subject to any disclaimer, the term of this patent is extended or adjusted under 35 U.S.C. 154(b) by 0 days.

(21) Appl. No.: 19/001,010

(22) Filed: Dec. 24, 2024

(51) Int. Cl.
*A01H 5/08* (2018.01)
*A01H 6/74* (2018.01)

(52) U.S. Cl.
USPC ..... Plt./209
CPC ..... *A01H 6/7409* (2018.05)

(58) Field of Classification Search
USPC ..... Plt./209, 208
CPC ..... A01H 5/08; A01H 5/00; A01H 6/7409; A01H 6/74
See application file for complete search history.

*Primary Examiner* — June Hwu
(74) *Attorney, Agent, or Firm* — Seckel IP, PLLC

(57) ABSTRACT

A new variety of strawberry plant named 'HOB-R490' that has high hardness of fruit body, with the fruit having a medium size and a light red core.

3 Drawing Sheets

Common name: Strawberry.
Botanical classification: *Fragaria* x *ananassa* Duchesne ex Rozier.
Variety denomination: 'HOB-R490'.

CROSS-REFERENCE TO PRIOR APPLICATION

This application follows Japanese plant variety rights application No. 37438 filed May 24, 2024, the entire content of which is incorporated by reference herein.

BACKGROUND OF THE NEW VARIETY

The present invention relates to a new and distinct variety of strawberry, *Fragaria* x *ananassa* Duchesne ex Rozier, which has been given the variety denomination 'HOB-R490'.

The variety is distinguished by its high hardness of fruit body, with the fruit having achenes positioned deep below the surface and a light red core, that distinguish it notably from its female parent 'Pechika Pure' (fruit having achenes positioned shallow below the surface and a yellowish pink (RHS 33C) core).

ORIGIN OF THE VARIETY

The parent varieties are 'R392-43' (male parent) (not patented in the U.S.) and 'Pechika pure' (female parent) (not patented in the U.S.).

The variety was asexually reproduced by runners in Higashikagura-cho, Kamikawa-gun, Hokkaido, Japan.

In March 2021, the male variety 'R392-43' and female variety 'Pechika pure' were crossed in a greenhouse in Higashikagura-cho, Kamikawa-gun, Hokkaido, Japan.

In 2021, the resulting seedlings were sown and raised.

In 2022, the raised seedlings were planted and grown in a test field located in Higashikagura-cho, Kamikawa-gun, Hokkaido, Japan, and two individuals with superior characteristics were selected.

In 2023, the test was carried out again, and 'HOB-R490' was selected for its high hardness of fruit body and its taste.

On May 24, 2024, an application for plant variety rights No. 37438 was filed for the present variety in the Japanese Plant Variety Protection Office of the Ministry of Agriculture, Forestry and Fisheries (MAFF), Japan.

Cultivation of the variety does not require special conditions or treatments.

Proper planting time is from the end of March to the beginning of April.

Flowering time is from the middle of May.

Harvesting time is from the end of June to the end of November.

The variety is currently mainly intended for fruit production.

SUMMARY OF THE VARIETY

The variety is distinguished by its high hardness of fruit body and rich taste with strong sweetness and acidity, with the fruit having a light red (RHS 40C) core, that distinguish it notably from its female parent 'Pechika Pure' (fruit having a yellowish pink (RHS 33C) core). The variety is also distinguished by its upright plant growth habit and cylindrical fruit shape, which distinguish it notably from its male parent 'R392-43' (semi-upright plant growth habit and conical fruit shape).

A comparison table with the male parent 'R392-43' is as follows (evaluation based on averages).

TABLE 1

| | HOB-R490 | R392-43 |
|---|---|---|
| Plant: growth habit | upright | semi-upright |
| Fruit: shape | rhombic | conical |

A comparison table with the female parent 'Pechika Pure' is as follows (evaluation based on averages).

TABLE 2

| | HOB-R490 | Pechika Pure |
|---|---|---|
| Color of core | Light red (RHS 40C) | yellowish red (RHS 33C) |

A comparison table with comparative variety '378-104' is as follows (evaluation based on averages).

TABLE 3

| | HOB-R490 | 378-104 |
|---|---|---|
| Plant: growth habit | upright | semi-upright |
| Fruit: cavity | absent or small | medium |

BRIEF DESCRIPTION OF THE DRAWINGS

In the accompanying drawings, which are as nearly true as is reasonable possible to make in a color illustration of this type.

Figure 1:
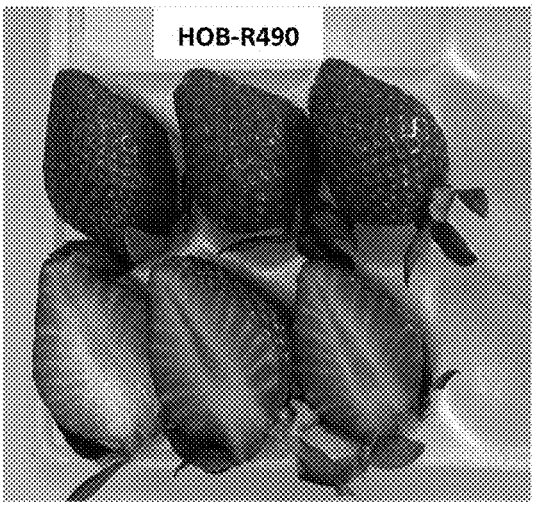
FIG. 1 is a color photograph showing the whole fruit of 'HOB-R490' at the top and a cross-section of the fruit of 'HOB-R490' at the bottom.
Figure 2:
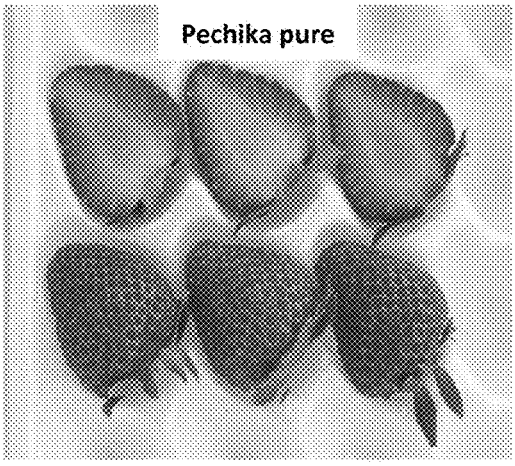
FIG. 2 is a color photograph showing cross-sections of the fruit of 'Pechika Pure' at the top and the whole fruit of 'HOB-R490' at the bottom.
Figure 3:
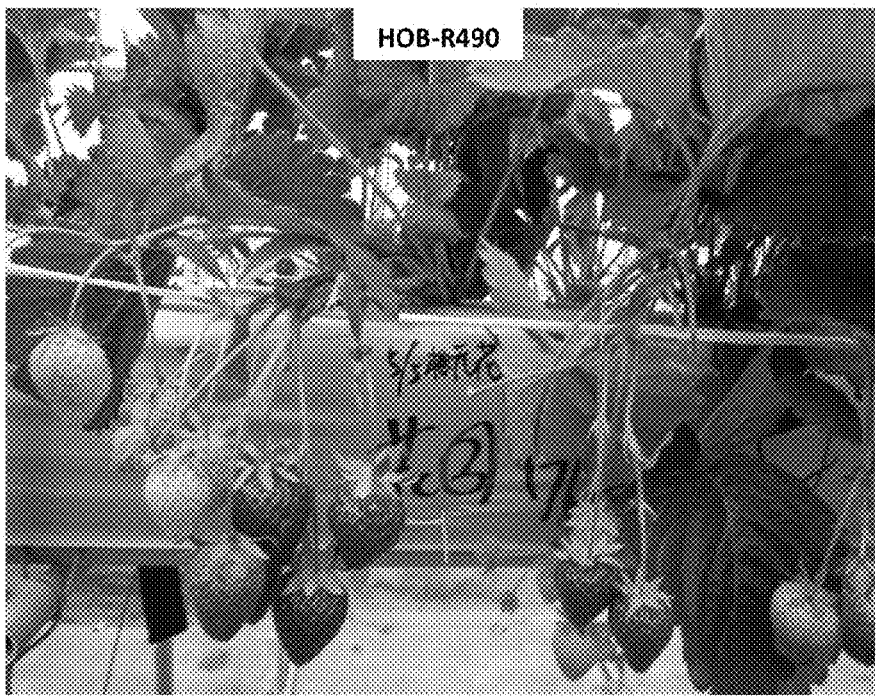
FIG. 3 is a color photograph showing the plant, leaves, and fruit of 'HOB-R490'.
Figure 4:
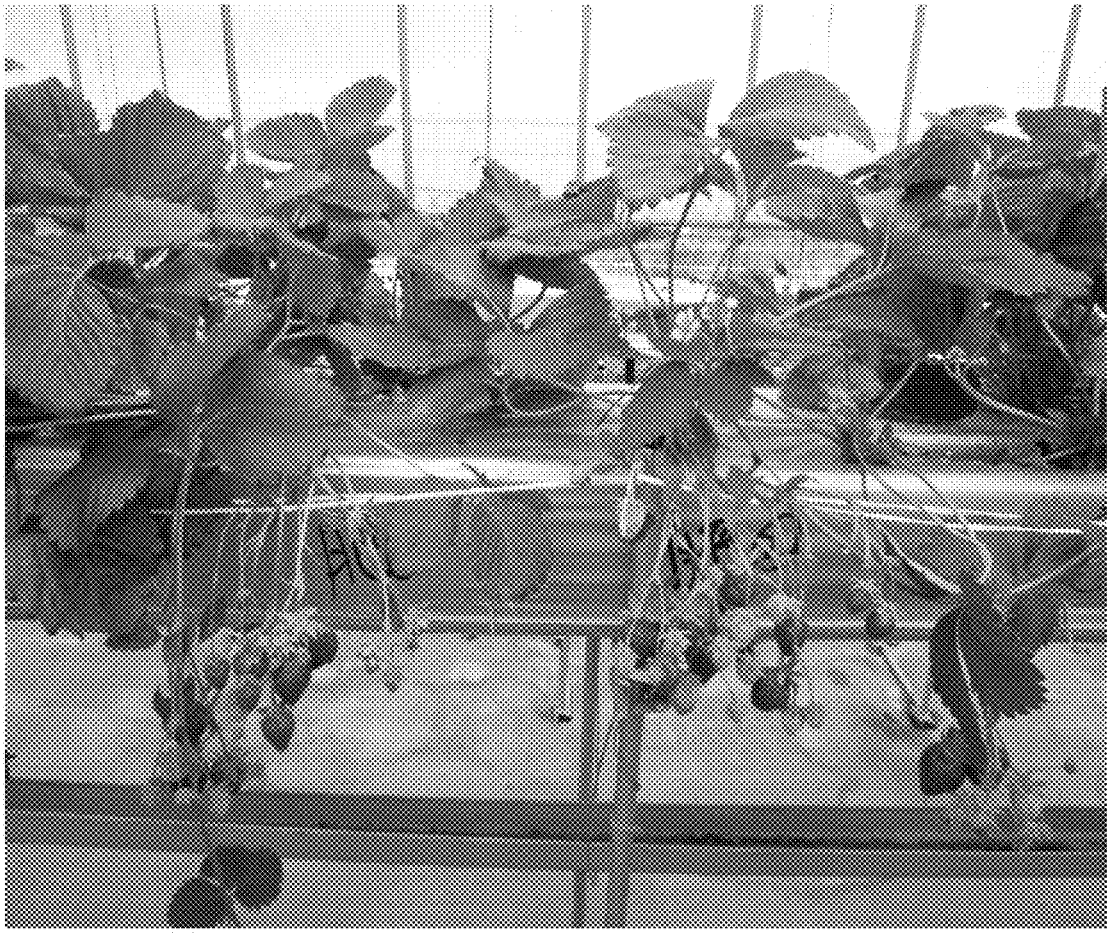
FIG. 4 is a color photograph showing the plant, leaves, and fruit of 'HOB-R490'.
Figure 5:
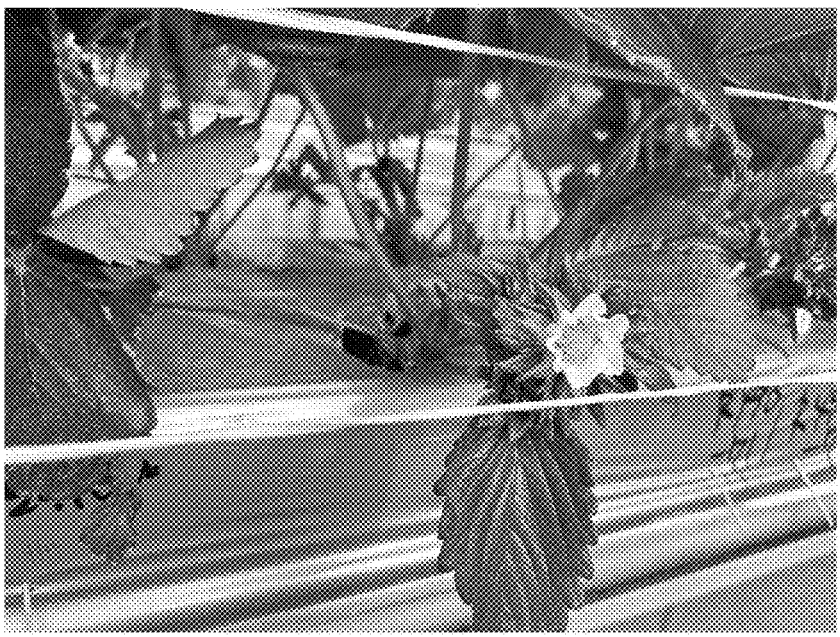
FIG. 5 is a color photograph showing the flower of 'HOB-R490'.
Figure 6:
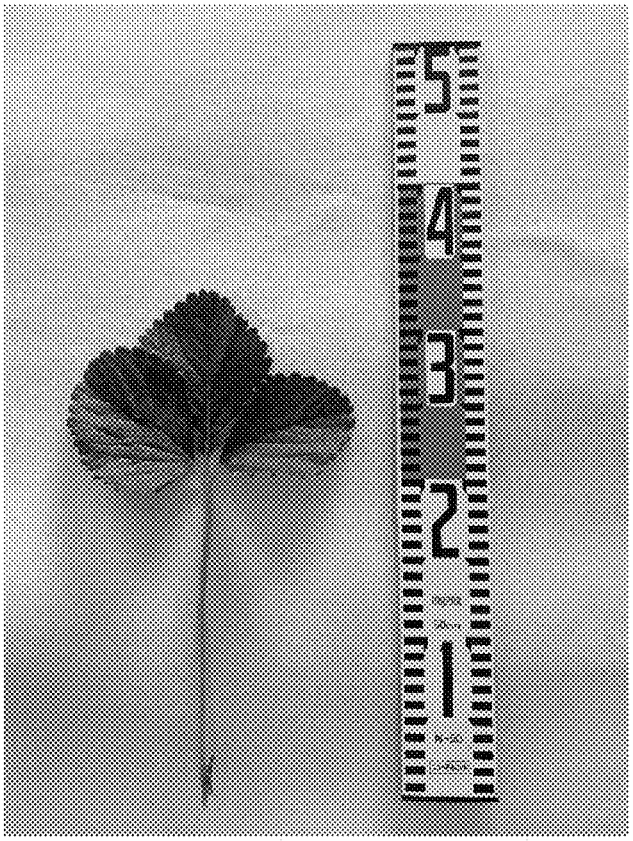
FIG. 6 is a color photograph showing the leaf of 'HOB-R490'.

Due to chemical and/or digital development, processing and printing, the plants or portions of plants depicted in the photographs may or may not be precisely accurate, when compared to the actual botanical specimens.

DETAILED DESCRIPTION OF THE INVENTION

The botanical description and the photographs are of the 'HOB-R490' plants evaluated in 2023, including for the comparison with the female parent 'Pechika Pure'. Values as provided are averages.

The plants shown on the photographs were grown in Higashikagura-cho, Kamikawa-gun, Hokkaido, Japan. The plant is a 5-year grown plant.

Colors are given according to the RHS (Royal Horticultural Society) Colour Chart (Fourth Ed., 2001).

BOTANICAL DESCRIPTION

TABLE 4

| | Characteristics | States/Values |
|---|---|---|
| 1 | Plant | |
| 1.1 | Plant growth habit | upright |
| 1.2 | Density of foliage | medium to dense |
| 1.3 | Vigor | medium to strong |
| 1.4 | Number of axillary bud | few |
| 1.5 | Position of inflorescence in relation to foliage | same level |
| 1.6 | Number of stolons | medium to few |

TABLE 4-continued

| | Characteristics | States/Values |
|---|---|---|
| 1.7 | Stolon average length | 25 cm |
| 1.8 | Stolon surface texture | rough |
| 1.9 | Stolon color | strong yellow green (RHS 142A) |
| 2 | Leaf | |
| 2.1 | Leaf size | medium to large (length: 31.3 $cm^2$ (length 25 cm, width 31 cm) |
| 2.2 | Color of upper side | dark green (RHS146A) |
| 2.3 | Color of lower side | brilliant yellowish green (RHS 134C) |
| 2.4 | Glossiness | weak |
| 2.5 | Blistering | strong |
| 2.6 | Variegation | absent |
| 2.7 | Terminal leaflet: size | large (223 $cm^2$) (length 17 cm, width 14 cm) |
| 2.8 | Shape of base | acute |
| 2.9 | Margin | serrate to crenate |
| 2.10 | Shape in cross section | concave |
| 3 | Stem | |
| 3.1 | Petiole length | medium to short (20.3 cm) |
| 3.2 | Petiole color | strong yellowish green (RHS 134B) |
| 3.3 | Attitude of hairs | slightly outwards |
| 3.4 | Anthocyanin coloration | absent or very weak |
| 3.5 | Peduncle: length | short (9.0 cm) |
| 3.6 | Peduncle: color | strong yellowish green (RHS 134B) |
| 3.7 | Pedicel: attitude of hairs | horizontal |
| 3.8 | Stipule: length | 2.0 cm |
| 4 | Flower | |
| 4.1 | Flower diameter | medium to large (3.5 cm) |
| 4.2 | Number of petals | 7 per flower |
| 4.3 | Arrangement of petals | free |
| 4.4 | Stamen | present |
| 4.5 | Petal: color of upper side | white (RHS N155D) |
| 4.6 | Petal: color of lower side | white (RHS NN155D) |
| 4.7 | Petal: shape | rounded |
| 5 | Fruit | |
| 5.1 | Fruit size | medium (31.8 g) (height 5.0 cm, diameter 4.0 cm) |
| 5.2 | Shape | rhombic |
| 5.3 | Shape at apex end | acute or flattened |
| 5.4 | Shape at calyx end | flattened |
| 5.5 | Color | red (RHS 41A) |
| 5.6 | Color of achenes | vivid purplish red (RHS N57A) |
| 5.7 | Evenness of color | even or very slightly |
| 5.8 | Evenness of surface | slightly uneven |
| 5.9 | Neck | absent |
| 5.10 | Position of calyx attachment | level with fruit |
| 5.11 | Calyx: diameter | 6.0 cm |
| 5.12 | Calyx: sepal number | 13 |
| 5.13 | Calyx: color designation | dark yellowish green (RHS N134A) |
| 5.14 | Attitude of sepals | upwards |
| 5.15 | Firmness | firm |
| 5.16 | Color of flesh | light red (RHS N34B) |
| 5.17 | Color of core | light red (RHS 40C) |
| 5.18 | Cavity | absent or small |
| 6 | Fruit ripening | |
| 6.1 | Time of beginning of flowering | medium to late (May 30) |
| 6.2 | Time of beginning of fruit ripening | June 19 |
| 6.3 | Type of bearing | day neutral |
| 6.4 | Soluble solids content | medium to high (Brix = 9) |
| 6.5 | Acidity | high (0.79%) |

Other features of the plant are as follows:

Plant hardiness zone of the plant: adapted to summer in cooler areas of Japan; has excellent heat resistance but poor cold resistance. In cold weather, the plants are dwarfed and the progress of fruit coloration is slow.

Pest and disease resistance: Normal resistance was observed for pests and diseases in Higashikagura-cho, Kamikawa-gun, Hokkaido, Japan.

We claim:

1. A new and distinct variety of strawberry plant named 'HOB-R490', substantially as described and illustrated herein.

* * * * *